(12) United States Patent
Hardesty

(10) Patent No.: US 7,344,304 B2
(45) Date of Patent: Mar. 18, 2008

(54) SELF-ALIGNMENT OF RADIOGRAPHIC IMAGING SYSTEM

(75) Inventor: Daniel M. Hardesty, Lincoln, CA (US)

(73) Assignee: Varian Medical Systems Technologies, Inc., Palo Alto, CA (US)

(*) Notice: Subject to any disclaimer, the term of this patent is extended or adjusted under 35 U.S.C. 154(b) by 0 days.

(21) Appl. No.: 11/153,001

(22) Filed: Jun. 14, 2005

(65) Prior Publication Data

US 2006/0280293 A1 Dec. 14, 2006

(51) Int. Cl.
*A61B 6/08* (2006.01)
(52) U.S. Cl. .......................................... 378/205; 378/62
(58) Field of Classification Search ........ 378/204–205, 378/62
See application file for complete search history.

(56) References Cited

U.S. PATENT DOCUMENTS

| 5,661,774 | A | * | 8/1997 | Gordon et al. ............... 378/101 |
| 5,920,070 | A | * | 7/1999 | Petrick et al. ......... 250/370.09 |
| 6,222,906 | B1 | * | 4/2001 | Sakaguchi et al. ......... 378/98.8 |
| 6,739,751 | B2 | * | 5/2004 | Williams ..................... 378/205 |
| 6,935,779 | B2 | | 8/2005 | Zhang et al. |
| 2002/0122531 | A1 | * | 9/2002 | Whitham ..................... 378/137 |
| 2003/0099328 | A1 | | 5/2003 | Jensen et al. |
| 2006/0067471 | A1 | * | 3/2006 | Hopkins et al. ........... 378/98.8 |

* cited by examiner

*Primary Examiner*—Edward J. Glick
*Assistant Examiner*—John M Corbett
(74) *Attorney, Agent, or Firm*—Foley & Lardner LLP

(57) ABSTRACT

An imaging system 10 is provided comprising an x-ray source 12, a detector 14, and an alignment device 38 adapted to align the detector 14 with the x-ray source 12 using an x-ray beam transmitted from the x-ray source 12. A method of positioning and aligning an imaging system is also provided.

10 Claims, 8 Drawing Sheets

SELF-ALIGNMENT OF RADIOGRAPHIC IMAGING SYSTEM

FIELD OF THE INVENTION

This invention relates generally to radiographic imaging systems and methods, and in particular, to systems and methods for automatically positioning and aligning radiographic imaging systems.

BACKGROUND

Radiographic imaging such as X-ray imaging has been used for a wide variety of applications in various fields. A typical x-ray imaging system includes an x-ray source generating x-ray beams to irradiate a region of interest (ROI), and an x-ray detector detecting the x-ray beams passing through the ROI. To achieve an x-ray image with sufficient information, precise positioning and alignment of the imaging system, especially between the x-ray source and detector, is required. In prior art imaging systems, the x-ray source and detector are physically attached to each other in a rigid and bulky structure such as an enclosed housing. In such imaging systems, the x-ray source and detector are aligned in fixed positions and typically not moveable relative to each other or able to repositioned and/or realigned.

U.S. Pat. No. 6,282,264 describes a method of positioning a digital flat panel in an x-ray imaging system. While the x-ray source and detector are moveable relative to each other, the detector is mechanically connected with an x-ray tube and the alignment of the imager with the x-ray tube is achieved by moving the imager through pre-defined ranges of motion in a known coordinate system physically installed in an examination room.

There are instances that it is necessary to examine or inspect objects such as a suspicious container in a non-destructive way to not trigger, for example, an explosive that might be concealed inside the container. There are also instances that it is impractical to move objects such as a pipeline in use to an examination room for inspection. It is desirable to have a portable x-ray imaging system in these instances so that an x-ray source and a detector can be conveniently positioned, readily moveable and adjusted. Accordingly, there is a need to automatically align an x-ray source and a detector without mechanical linkage for optimum performance of an imaging system.

SUMMARY OF THE INVENTION

An imaging system is provided comprising an x-ray source, a detector, and an alignment device adapted to align the detector with the x-ray source using an x-ray beam transmitted from the x-ray source. A method of positioning and aligning an imaging system is also provided.

BRIEF DESCRIPTION OF THE DRAWINGS

These and various other features and advantages of the present invention will become better understood upon reading of the following detailed description in conjunction with the accompanying drawings and the appended claims provided below, where:

DETAILED DESCRIPTION OF THE INVENTION

Figure 1:
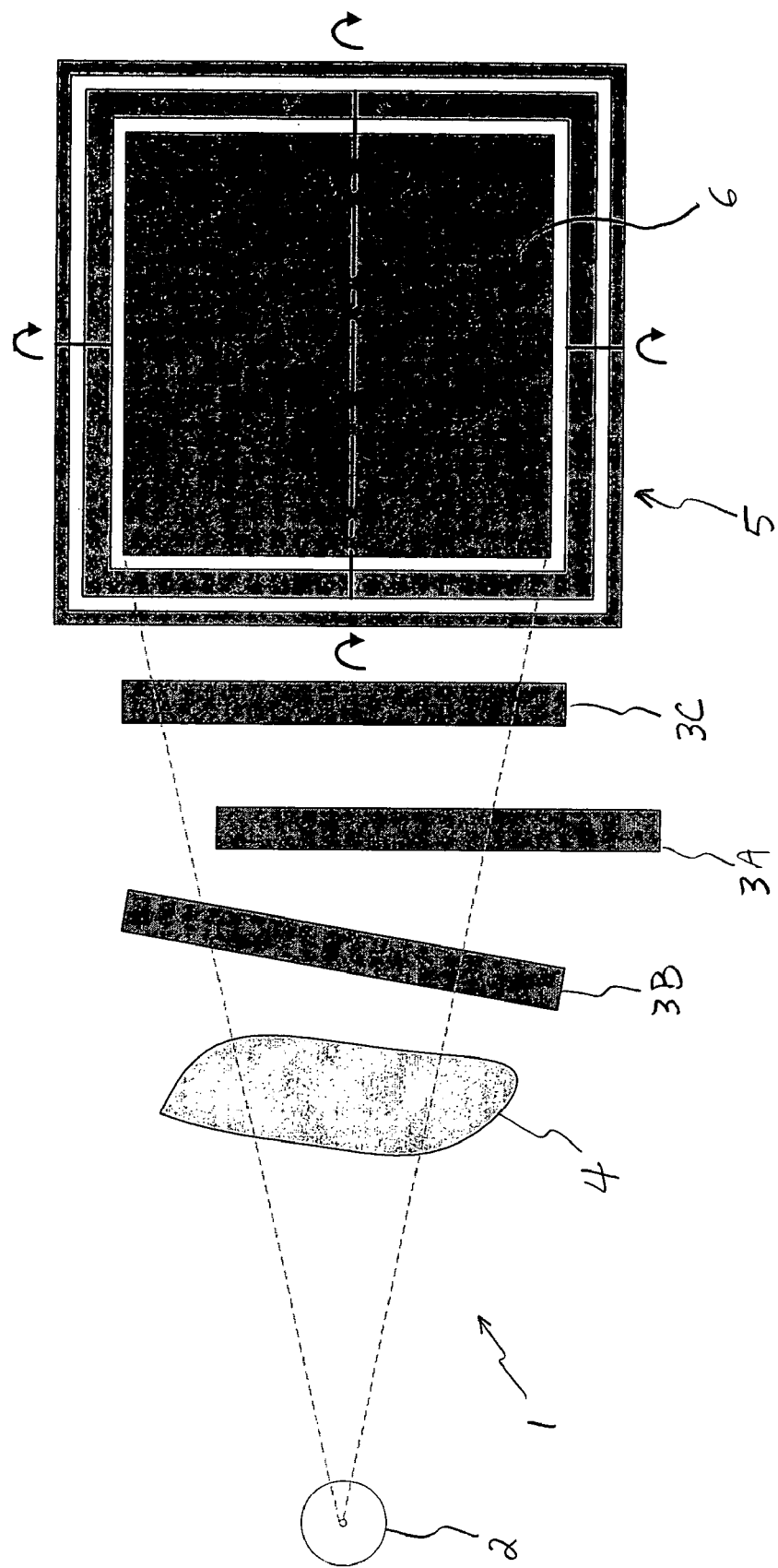
FIG. 1 is a schematic illustrating a properly positioned and aligned detector, an improperly positioned detector, and a misaligned detector in an x-ray imaging system.

Various embodiments of the present invention are described hereinafter with reference to the figures. It should be noted that the figures are not drawn to scale and elements of similar structures or functions are represented by like reference numerals throughout the figures. It should also be noted that the figures are only intended to facilitate the description of specific embodiments of the invention. They are not intended as an exhaustive description of the invention or as a limitation on the scope of the invention. In addition, an aspect described in conjunction with a particular embodiment of the present invention is not necessarily limited to that embodiment and can be practiced in any other embodiments of the present invention. For instance, in the following description, the present invention is described with embodiments of an x-ray imaging system. It will be appreciated that the claimed invention can be used not only for x-ray imaging systems, but also for any other type of radiographic imaging systems such as infrared ray, visible ray, and ultraviolet ray imaging systems. Further, in the following description, the present invention is described with embodiments of two-dimensional images shown on a display. It will be appreciated that the claimed invention can be used in an imaging system where three- or four-dimensional images are formed, for instance, using a cone beam technology.

The present invention provides a method of positioning and/or aligning an imaging system. As used herein, the term "positioning" refers to an act of adjusting the location of an x-ray source and/or a detector in an x-ray field. The term "aligning" refers to an act of adjusting the orientation of a detector and/or an x-ray source so that the x-ray source is normal to the surface of the detector. FIG. 1 schematically illustrates an imaging system 1 including an x-ray source 2 and a detector 3 with a position error 3A, a misalignment 3B, and a proper position and alignment 3C. An image 6 of an object 4 is shown on a display 5.

Figure 2:
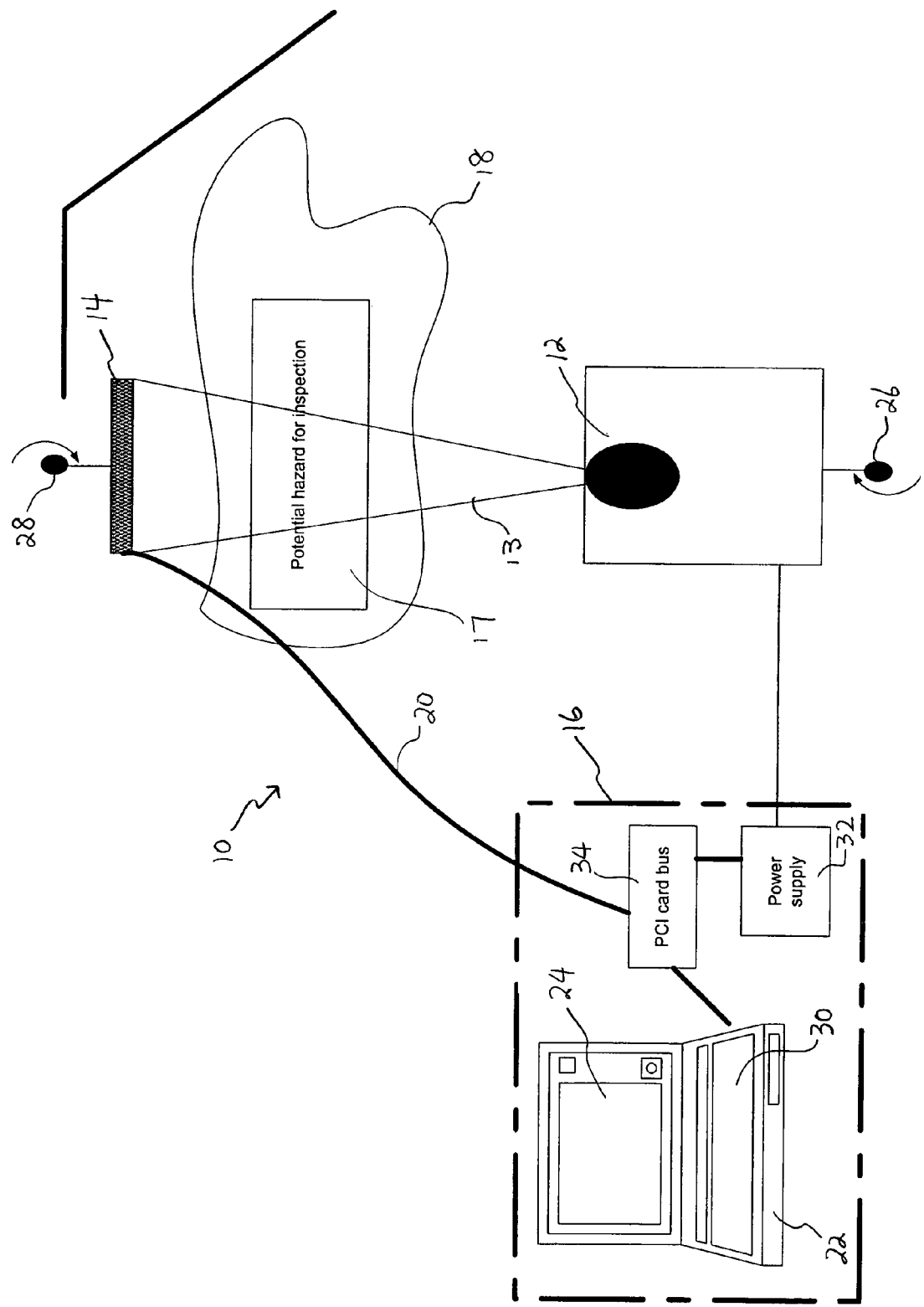
FIG. 2 is a schematic illustrating an x-ray imaging system in accordance with an embodiment of the present invention.

An imaging system 10 in accordance with an embodiment of the present invention is illustrated in FIG. 2. The imaging system 10 is a portable, self-contained x-ray imaging system that can digitally process, display, store and/or transmit electronic x-ray images of a region of interest in an object in real time. The x-ray imaging system 10 includes an x-ray source 12, a detector 14, and a control station 16. Between the spaced apart x-ray source 12 and detector 14 is an object 18 to be examined or inspected. By way of example, the object 18 can be any object such as a patient, container, pipe, and any other item or region of interest to be investigated.

The x-ray source 12 generates and transmits an x-ray beam 13 to a region of interest 17 in the object 18. The x-ray detector 14 receives and detects the x-ray beam passing through the region of interest 17. The detector 14 can be a two-dimensional flat panel imager. The x-ray beam 13 is converted to electrical signals representing the intensity of the x-ray beams passing through the region of interest 17. The electrical signals are transmitted to the control station 16 via a signal cable 20, or alternatively, via wireless means (not shown). The electrical signals are processed in a process unit 22 in the control station 16 to form an image, which is displayed on a display 24. The imaging system 10 of the present invention can be a fluoroscopic imaging system, in which the x-ray source 12 scans any regions of interest 17 in the object 18 and the detector 14 detects the x-ray beams 13 and converts them to electrical signals to form and display images in real time.

The x-ray source 12 and detector 14 are supported in supporting structures such as articulated arms 26 and 28, respectively. Both the x-ray source 12 and the detector 14 can be translated, rotated, and/or tilted in any directions with manual and/or robotic motion control. In an embodiment of the present invention, the x-ray source 12 and detector 14 are independently controlled and not physically or mechanically connected to each other. In an alternative embodiment, the x-ray source 12 and the detector 14 are electronically connected and moved together after they are properly positioned and aligned.

The control station 16 can include a control unit 30 for actuating and/or controlling the detector 14 and/or x-ray source 12, a process unit 22 for processing the electrical signals transmitted from the detector 14, and a display unit 24 for displaying images formed. A power supply 32 can be included in the control station 16 for supplying power to the imaging system 10. Peripheral component interconnect (PCI) card bus 34 is included in the control station 16 for interfacing with the detector 14 and power supply 32. The control station 16 can be portable and self-contained in a suitcase.

Figure 3:
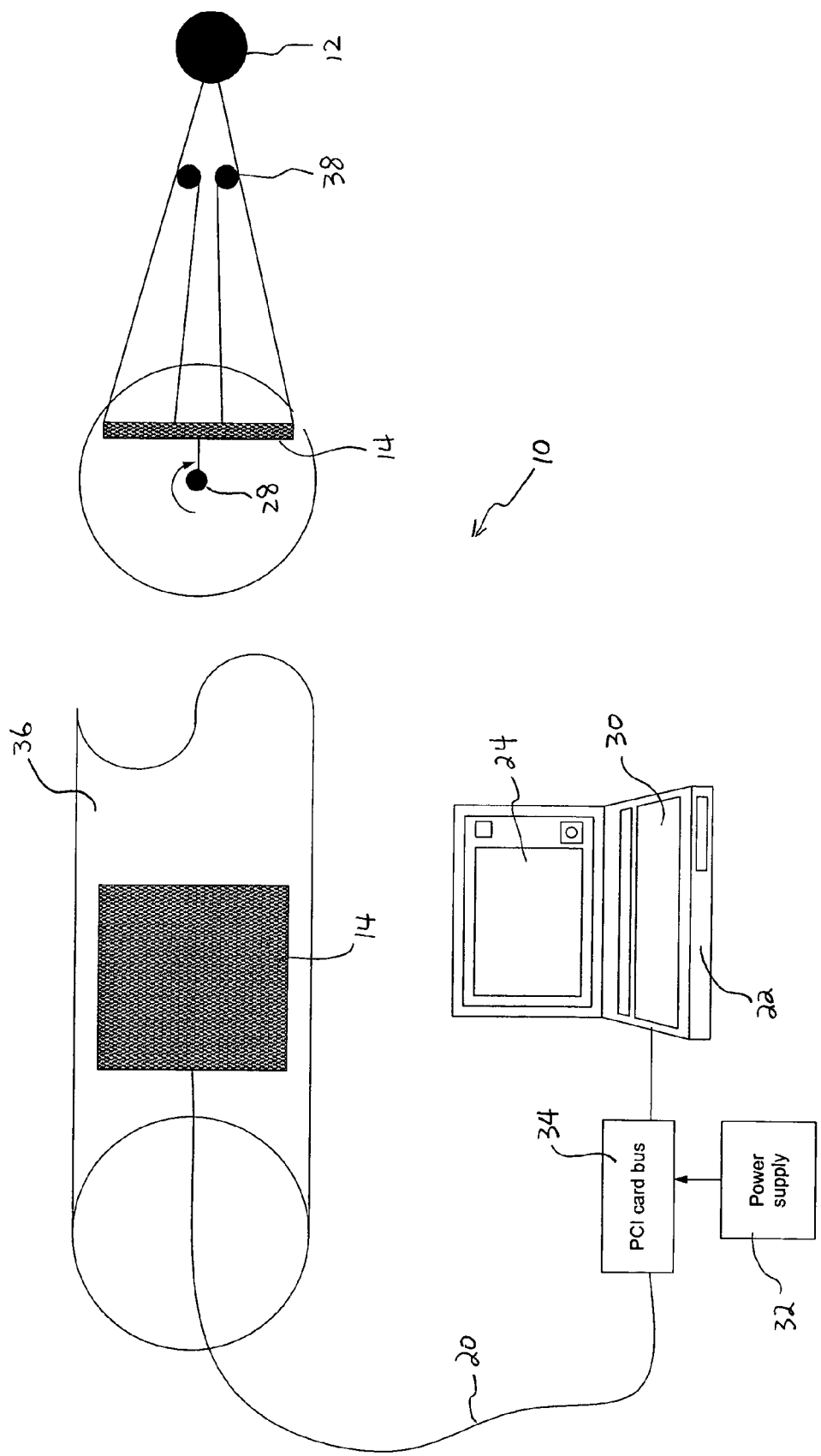
FIG. 3 is a schematic illustrating an x-ray imaging system including a reticle in accordance with an embodiment of the present invention.

FIG. 3 schematically illustrates an imaging system 10 in accordance with an embodiment of the present invention that can be used for inspecting, for example, the integrity of a plastic or metal pipe 36. The detector 14 is placed inside an enclosed area such as a pipe as illustrated. In this embodiment, the detector 14 is not physically and/or mechanically connected with the x-ray source 12. An alignment device 38 is used to align the detector 14 with the x-ray source 12.

Figure 4:
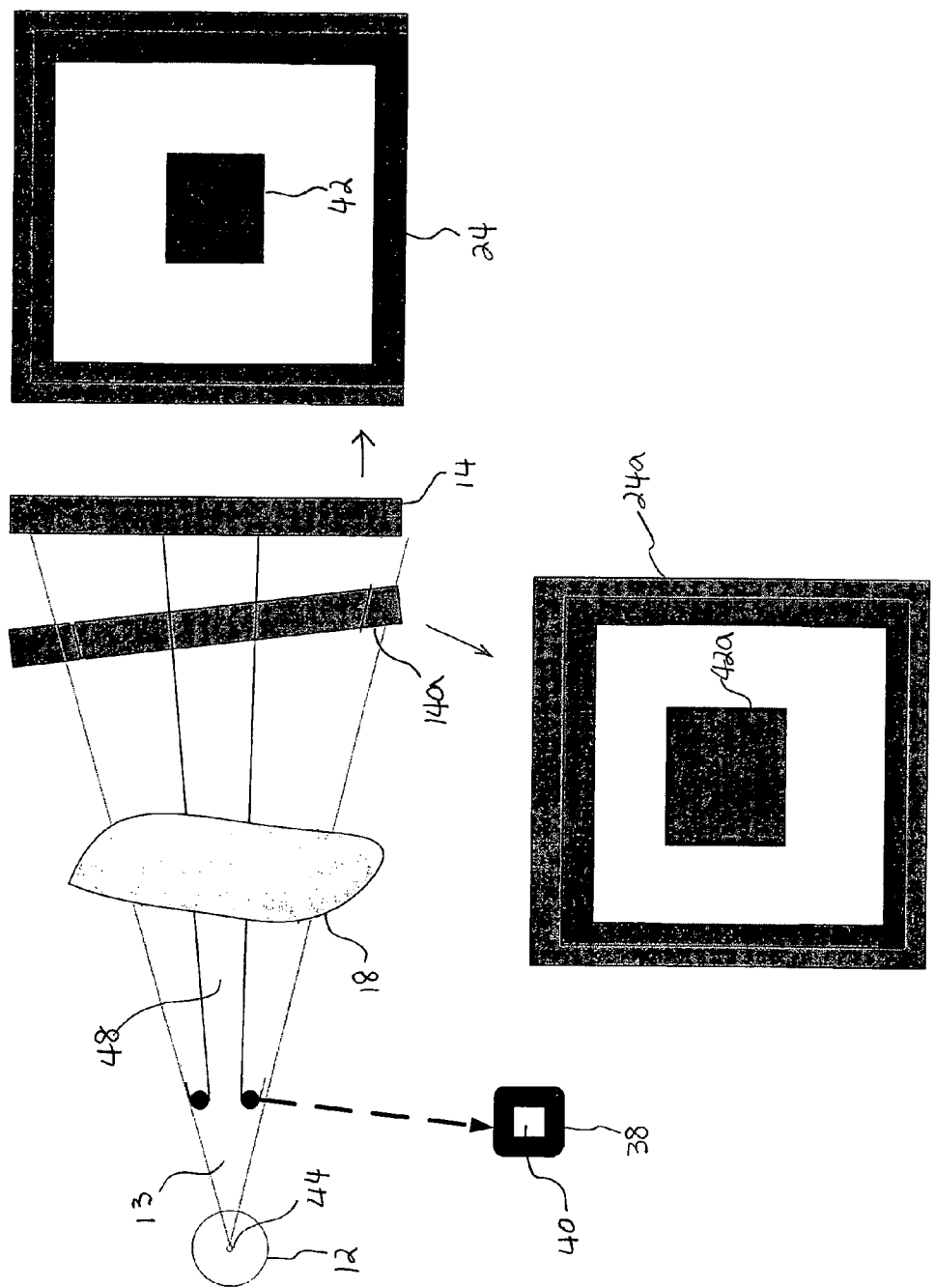
FIG. 4 is a schematic illustrating a reticle used in aligning a detector with an x-ray source in accordance with an embodiment of the present invention.

FIG. 4 schematically illustrates an alignment device 38 in accordance with an embodiment of the present invention. The alignment device 38 can be in the form of a reticle, which can be made of a heavy metal such as tungsten, or lead. An opening 40 is provided in the reticle 38. By way of example, the opening 38 shown in FIG. 4 is in the shape of a square and a square image 42 is formed on the display 24. Other shapes suitable for forming a unique and readily recognizable image such as a circle or star can also be used. For instance, the opening 40 in the reticle 38 can be an elongated slot, which allows the x-ray beam passing through to form an elongated band image on the display. Alternatively, the reticle can be a block having a plurality of small holes or openings forming a specific configuration, such as a square or circle.

The alignment reticle 38 can be attached to the x-ray source 12 at a distance from the focal point 44 of the x-ray source 12. In use, the x-ray source 12 transmits an x-ray beam 13 to the alignment reticle 38. A portion 48 of the x-ray beam 13 passes through the opening(s) 40 and irradiates the object 18 to be examined. The rest of the x-ray beam is blocked by the alignment reticle 38. The portion 48 of the x-ray beam passing through the opening(s) 40 and the object 18 is projected onto the detector 14, which converts the x-ray beam into electrical signals to form an image 42 on a display 24.

FIG. 4 illustrates an example of a misaligned detector 14a, which is tilted, with the upper portion of the detector closer to the x-ray source 12 and the lower portion farther from the x-ray source 12. The portion 48 of x-ray beam 48 passing through the alignment reticle 38 and object 18 is projected onto the misaligned detector 14a asymmetrically with respect to a pre-defined position, e.g., the center of the detector 14a due to magnification of the x-ray beam. For example, as shown in FIG. 4, the x-ray beam is projected closer to the upper edge and farther from lower edge of the detector 14a. The image 42a generated by the misaligned detector 14a is reflected on the display 24a, which is closer to an upper edge and farther from the lower edge of the display 24a.

The misaligned detector 14a can be then adjusted either manually or by remote control. For example, the detector 14a can be translated, rotated, and/or tilted during the adjustment. Alternatively, the x-ray source 12 can be independently translated, rotated, and/or tilted during the adjustment. The fluoroscopic imaging system makes possible of real-time display of images during the adjustment of the x-ray source 12 and/or the detector 14 in various orientations. By adjusting the orientation of the detector and/or the x-ray source, and determining the images shown on the display in real time, the detector can be properly aligned. Once the detector 14 is precisely aligned with the x-ray source 12, the projection of the x-ray beam 48 is on a pre-defined position, e.g., the center of the detector 14, which is reflected by an image 42 on a pre-defined position, e.g., the center of the display 24, as determined by for example, an equal distance of the image 42 to each side of the display 24.

Figure 5:
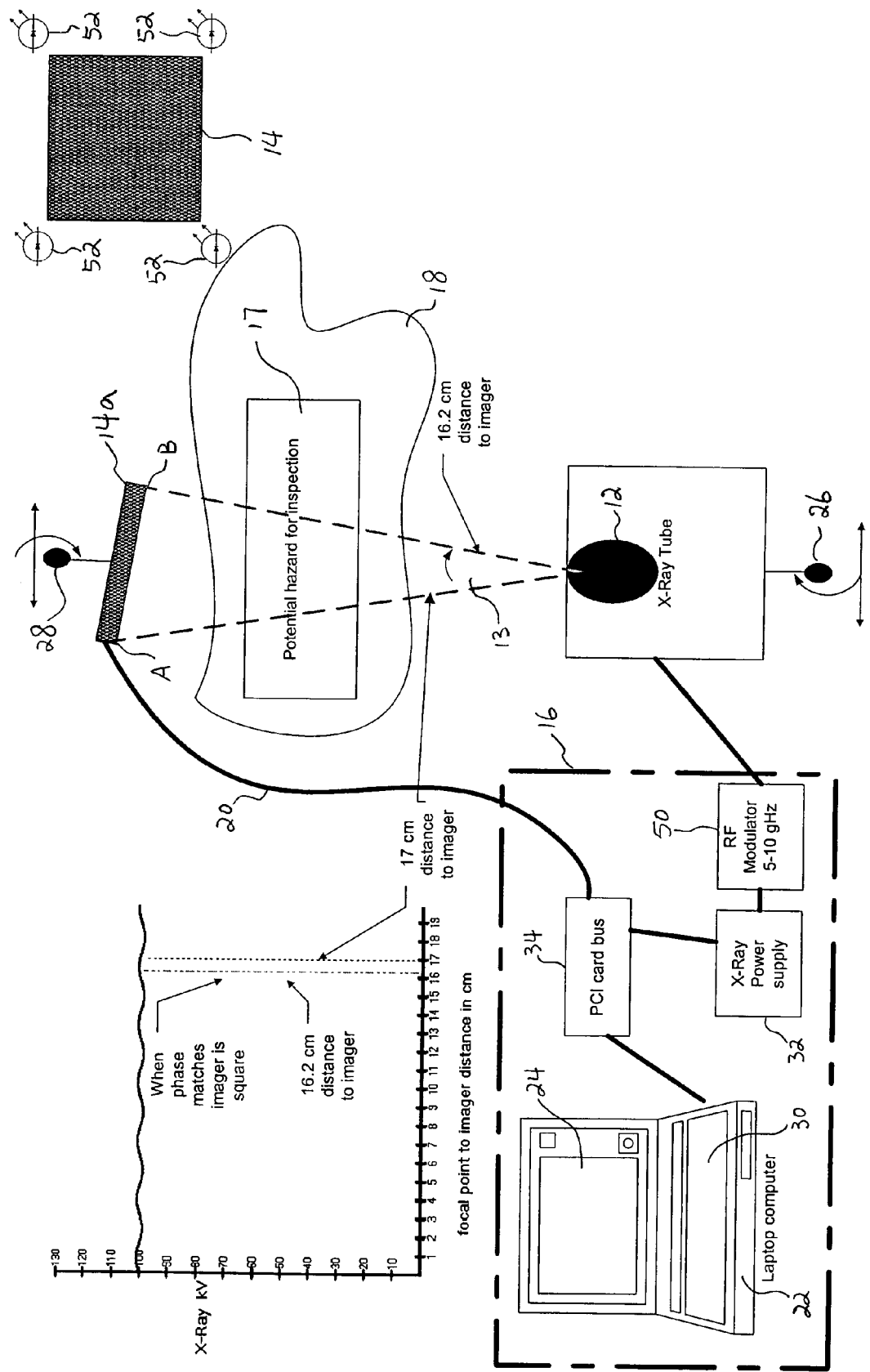
FIG. 5 is a schematic illustrating an x-ray imaging system including a radio frequency modulator in accordance with an embodiment of the present invention.

FIG. 5 illustrates an imaging system including a radio frequency (RF) modulator 50, which can be used to align the detector 14a with the x-ray source 12. As shown in FIG. 5, a modulator 50 is coupled to the x-ray source 12. The modulator 50 transmits a RF base wave having a frequency such as 5-10 gHz which modulates the voltage of an x-ray beam 13 generated by the x-ray source 12. The modulated x-ray beam passes through the object 18 and is received in the detector 14a. Two or more RF receivers 52 are coupled to the detector 14a to detect the phase angles of the RF base wave. FIG. 5 shows an example in which four RF receivers 52 are coupled to each of the four corners of the detector 14a. Alternatively, two or more RF receivers 52 can be coupled to each side of the detector 14a. In some embodiments, the RF receivers 52 can be integrated into the sensors and electronics of the detector 14a. The RF receivers 52 detect the phase angles of the base wave arrived at the RF receivers 52. If the detector is misaligned, as detector 14a illustrated in FIG. 5, the phase angles of the RF base wave arrived at different RF receivers 52 differ. Thus, by determining the phase angles of the RF base wave arrived at different spots on the detector, the alignment of the detector can be determined. For example, in the embodiment illustrated in FIG. 5, the phase angle of the base wave arrived at point A in the detector 14a is detected as θ1, indicating a distance between the x-ray source 12 and point A of 17 cm. The phase angle of the base wave arrived at point B is detected as θ2, indicating a distance between the x-ray source 12 and point B of 16.2 cm. Thus, the difference in phase angles between point A and B indicates the differences in distances between the x-ray source 12 and point A and between the x-ray source 12 and point B respectively, which in turns indicates a misalignment between the detector 14 and the x-ray source 12.

The misaligned detector 14a is then adjusted as described above, by translating, rotating, and/or tilting the detector. Alternatively, the x-ray source 12 can be independently translated, rotated, and/or tilted. Once the detector 14 is precisely aligned with the x-ray source 12, the phases angles of the RF base wave arrived at different spots in the detector 14 are equal, indicating equal distance between the x-ray source 12 and the different spots in the detector 14, which in turn indicates proper alignment of the detector 14 and the x-ray source 12.

Figure 6:
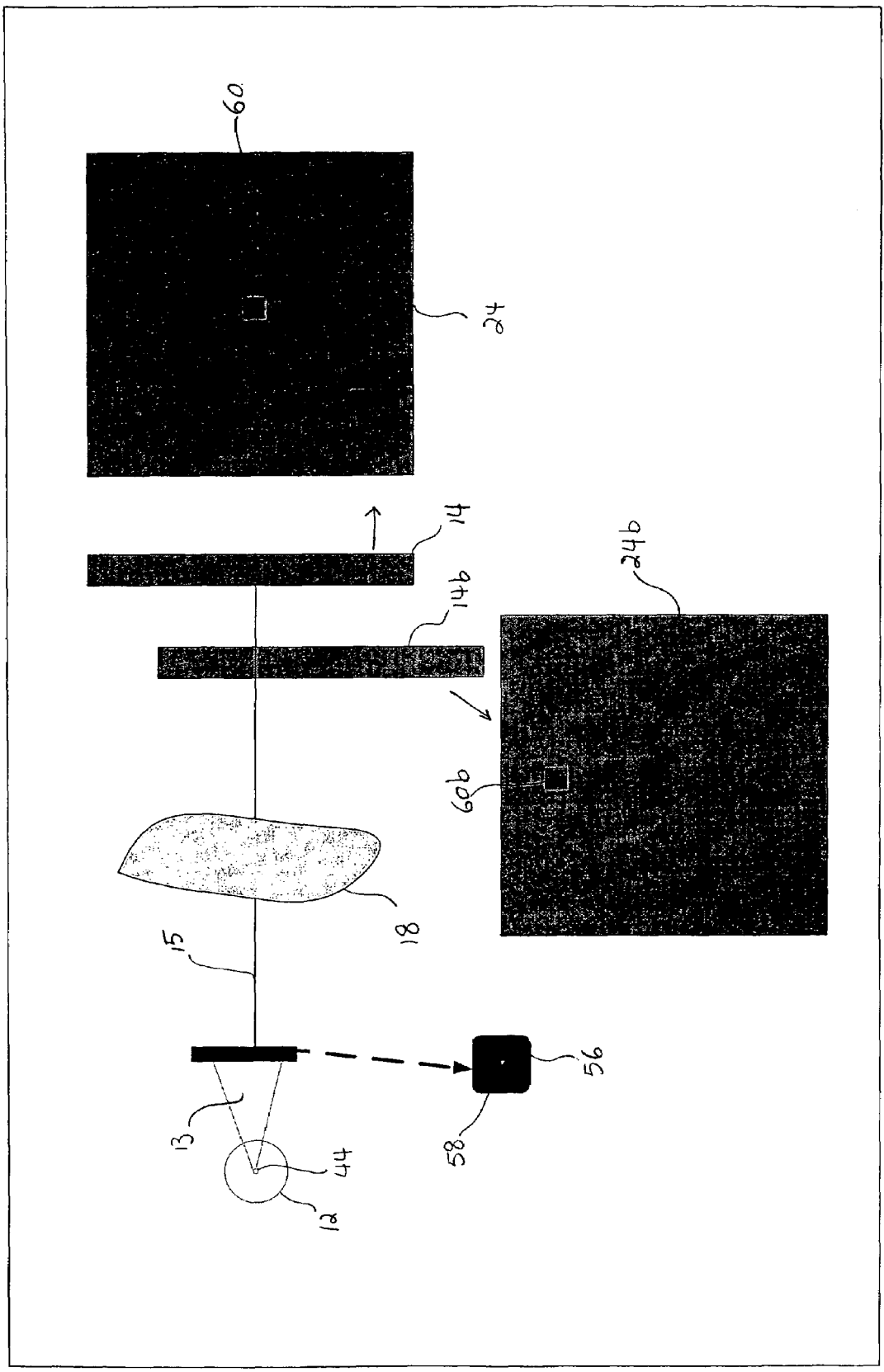
FIG. 6 is a schematic illustrating a reticle used in positioning a detector in accordance with an embodiment of the present invention.

FIG. 6 illustrates an embodiment of the present invention for positioning a detector in an x-ray field. As shown in FIG. 6, detector 14b is not properly positioned in an x-ray field. As a result of the improper positioning, detector 14b does not receive all of the x-ray beams passing through the region of interest in the object 18 and the image formed does not include sufficient information about the region of interest.

To properly position a detector 14 within an x-ray field, a positioning reticle 56 can be used. A small opening 52 is provided in the positioning reticle 56. The opening 52 is substantially smaller than the size of the detector 14. The opening 52 can be in any unique shape that can form an image readily recognizable in the display. The reticle 56 is placed at a distance from the focal point 44 and blocks all x-ray beam transmitted from the x-ray source 12 except a small portion 15 through the small opening 52 in the reticle 56.

When the detector 14b is not properly positioned in an x-ray field, the projection of the x-ray beam passing through the small reticle is off a pre-defined position, e.g., the center of the detector 14b. This can be readily recognized by an image off a pre-defined position, e.g., an off-center image 60b formed on the display 24b. The detector 14b is then adjusted either manually or by remote control, for example, by translating the detector in a plane. Alternatively, the x-ray source 44 can be independently translated in a plane in a search mode. The fluoroscopic imaging system used in the present invention makes possible of real-time display of images generated during the adjustment of the detector 14 and/or x-ray source 12 in various positions. By adjusting the detector and/or the x-ray source, and determining the images shown on the display, the detector can be properly positioned in the x-ray field. Once the detector 14 is properly positioned in the x-ray field, the projection of the x-ray beam 15 is on the pre-defined position, e.g., the center of the detector 14, which is indicated by an image 60 in the pre-defined position, e.g., the center of the display 24.

Figure 7:
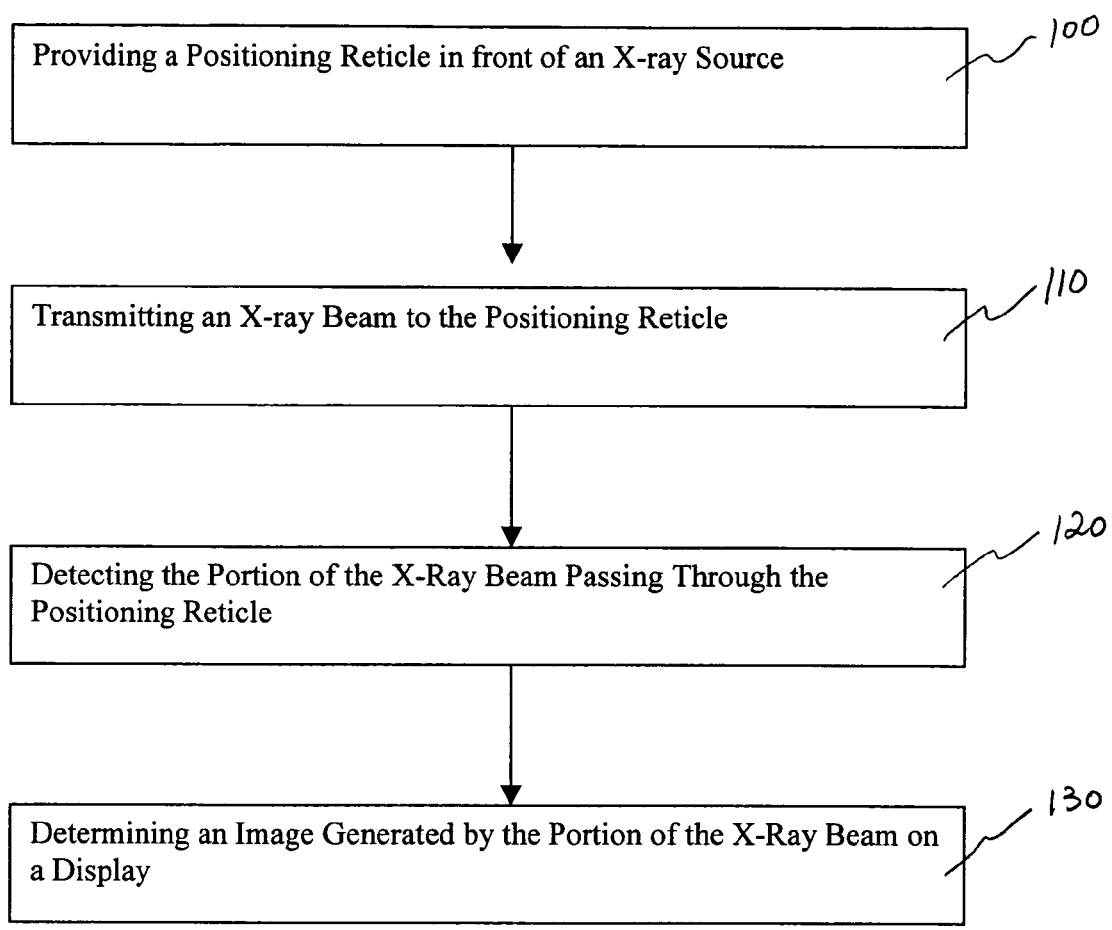
FIG. 7 is a block diagram illustrating a method of positioning a detector with an x-ray source in accordance with an embodiment of the present invention.

FIG. 7 illustrates a block diagram showing a method of positioning an imaging system in accordance with one embodiment of the present invention. At step 100, a positioning reticle is provided in front of an x-ray source. The positioning reticle is provided with an opening that is substantially smaller than the size of the detector so that only a small portion of an x-ray beam passes through the positioning reticle. The size of the opening can be selected based on specific applications. At step 110, the x-ray source is actuated and transmits an x-ray beam to the positioning reticle. The x-ray beam is blocked by the positioning reticle except for a small portion of the beam, which passes through the opening in the reticle to a region of interest. The portion of the x-ray beam is received and detected in the detector as shown in step 120, which converts the x-ray beam to electrical signals representing the intensity of the x-ray beam passing through the object of the interest. At step 130, the image formed by the electrical signals is determined as to its position or location on the display. If the image is not in the pre-defined position, e.g., center of the display, the detector and/or the x-ray source is adjusted by for example translating the detector and/or x-ray source in a plane. Then steps 100-130 are repeated until the image is in the pre-defined position, e.g., the center of the display.

Figure 8:
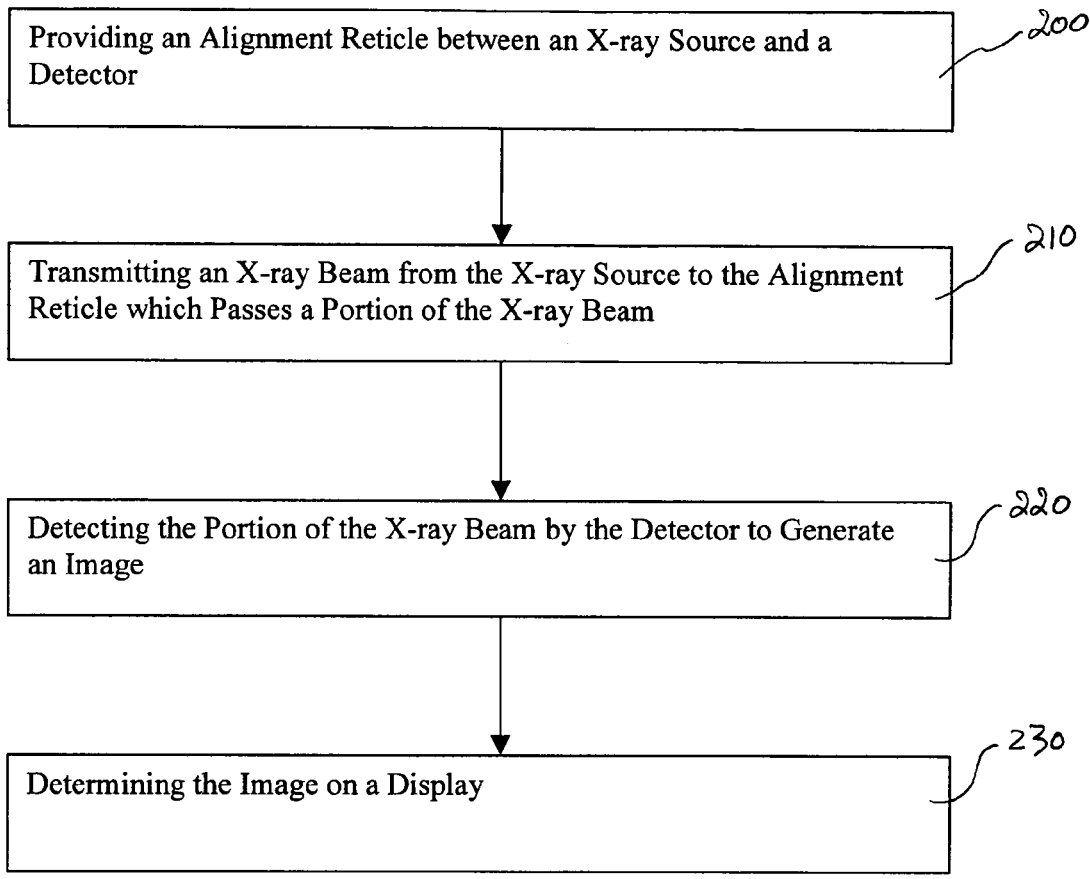
FIG. 8 is a block diagram illustrating a method of aligning a detector with an x-ray source in accordance with an embodiment of the present invention.

FIG. 8 illustrates a block diagram showing a method of aligning a detector with an x-ray source in accordance with an embodiment of the present invention. At step 200, an alignment reticle is provided in front of an x-ray source. The alignment reticle is provided with an opening to allow a portion of an x-ray beam passing therethrough. The opening can be in the shape of a square, an elongated slot, a circle etc. Alternative, the alignment reticle is a block having a plurality of holes or openings forming a readily determinable configuration such as a square or circle. At step 210, the x-ray source is actuated and transmits an x-ray beam to the alignment reticle. A portion of the x-ray beam passes through the opening in the reticle to a region of interest. The x-ray beam passing through the region of interest is received and detected in the detector as shown at step 220, which converts the x-ray beam to electrical signals representing the intensity of the x-ray beam passing through the object of the interest. At step 230, the image formed by the electrical signals is determined as to its location on the display. If the image is not at the pre-defined position, e.g., the center of the display, the detector and/or the x-ray source are adjusted by for example translating, rotating and/or tilting. Then steps 200-230 are repeated until the image is on the pre-defined position, e.g., the center of the display.

Figure 9:
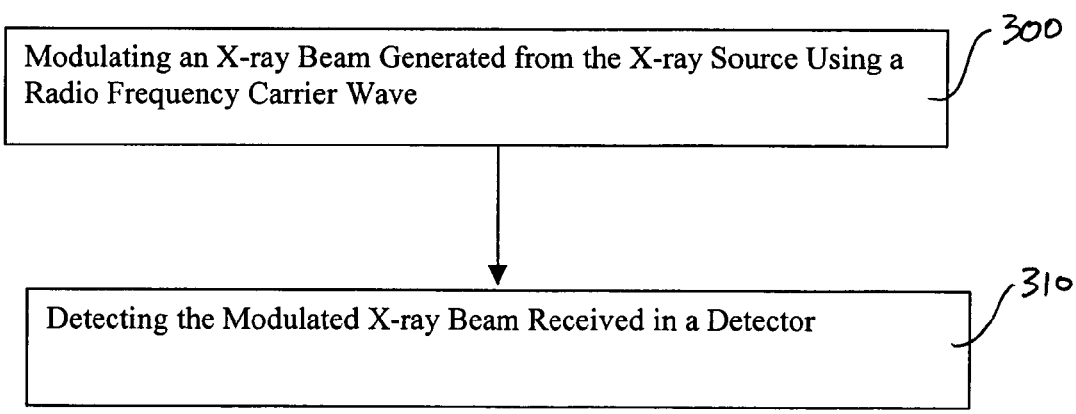
FIG. 9 is a block diagram illustrating a method of aligning a detector with an x-ray source in accordance with another embodiment of the present invention.

FIG. 9 illustrates a block diagram showing a method of aligning an imaging system in accordance with another embodiment of the present invention. At step 300, an x-ray beam is modulated by a radio frequency base wave. At step 310, the phase angles of the modulated beam are detected by two or more RF receivers provided in the detector. If the phase angles of the RF base wave arrived at the two or more RF receivers are different, the detector and/or x-ray source are adjusted by translating, rotating and/or tilting. The steps 300-310 are repeated until the phase angels are equal.

From the foregoing it will be appreciated that, although specific embodiments of the invention have been described herein for purposes of illustration, various modifications may be made without deviating from the spirit and scope of the invention.

What is claimed is:

1. An imaging system comprising an x-ray source, a detector, and an alignment device adapted to align the detector with the x-ray source using an x-ray beam transmitted from the x-ray source, wherein the alignment device comprises a radio frequency (RF) modulator coupled to the x-ray source for modulating an x-ray beam, and a plurality of RF sensors coupled to the detector for detecting the modulated x-ray beam.

2. The imaging system of claim 1 wherein the detector comprises a two-dimensional flat imager and said alignment device includes two or more RF sensors coupled to the imager.

3. The imaging system of claim 1 wherein the plurality of RF sensors are integral of the detector.

4. A portable imaging system comprising an x-ray source and a detector movable relative to each other, and an alignment device adapted to align the detector with the x-ray source using an x-ray beam transmitted from the x-ray source, wherein the alignment device comprises a radio frequency (RE) modulator coupled to the x-ray source for modulating an x-ray beam, and a plurality of RE sensors coupled to the detector for detecting the modulated x-ray beam.

5. A method of aligning an imaging system including an x-ray source and a detector moveable relative to each other, comprising the steps of:
   modulating an x-ray beam generated from the x-ray source using a radio frequency carrier wave;
   detecting the modulated x-ray beam received in said detector, and
   aligning the detector with the x-ray source using a plurality of RF sensors coupled to the detector for detecting the modulated x-ray beam.

6. The method of claim 5 wherein the modulating step comprises modulating a voltage of an x-ray beam.

7. The method of claim 5 wherein the detecting step comprises determining a phase angle of the radio frequency carrier wave received in the detector.

8. The method of claim 7 wherein the detecting step comprises determining a phase angle of the carrier wave received at at least two locations in the detector.

9. The method of claim 8, further comprising the step of adjusting the detector and/or x-ray source such that the phase angle of the carrier wave received at at least two locations of the detector is substantially equal.

10. The method of claim 8 wherein the detector is a two-dimensional flat panel detector, and said detecting step comprises determining a phase angle of the carrier wave received at each of four corners or edges of the detector.

* * * * *

UNITED STATES PATENT AND TRADEMARK OFFICE
CERTIFICATE OF CORRECTION

PATENT NO. : 7,344,304 B2 Page 1 of 1
APPLICATION NO. : 11/153001
DATED : March 18, 2008
INVENTOR(S) : Daniel M. Hardesty It is certified that error appears in the above-identified patent and that said Letters Patent is hereby corrected as shown below:

IN THE CLAIMS:

Claim 4, column 7, line 12, please replace "RE" with -- RF --.

Claim 4, column 7, line 13, please replace "RE" with -- RF --.

Signed and Sealed this

Twenty-sixth Day of August, 2008

JON W. DUDAS
*Director of the United States Patent and Trademark Office*